US005695500A

United States Patent [19]
Taylor et al.

[11] Patent Number: 5,695,500
[45] Date of Patent: Dec. 9, 1997

[54] SYSTEM FOR MANIPULATING MOVEMENT OF A SURGICAL INSTRUMENT WITH COMPUTER CONTROLLED BRAKE

[75] Inventors: Russell Highsmith Taylor, Ossining, N.Y.; Yong-yil Kim, Seoul, Rep. of Korea

[73] Assignee: International Business Machines Corporation, Armonk, N.Y.

[21] Appl. No.: 223,969

[22] Filed: Apr. 6, 1994

Related U.S. Application Data

[62] Division of Ser. No. 147,008, Nov. 2, 1993, which is a continuation of Ser. No. 714,816, Jun. 13, 1991, abandoned.

[51] Int. Cl.$^6$ ................................................ A61B 19/00
[52] U.S. Cl. .................................................... 606/130
[58] Field of Search ............................ 606/130, 54, 58, 606/61, 19, 4, 1

[56] References Cited

U.S. PATENT DOCUMENTS

| | | | |
|---|---|---|---|
| 1,664,210 | 3/1928 | Hall | 128/782 |
| 2,119,649 | 6/1938 | Roosen | 128/630 |
| 2,315,160 | 3/1943 | Newstedt et al. | 128/70 |
| 3,262,452 | 7/1966 | Hardy et al. | 606/130 |
| 3,273,559 | 9/1966 | Evans | 128/775 |
| 3,282,152 | 11/1966 | Myer | 128/774 |
| 3,338,235 | 8/1967 | Gordon | 606/130 |
| 3,359,583 | 12/1967 | Strube | 269/58 |
| 3,480,002 | 11/1969 | Flaherty et al. | 128/606.06 |
| 3,481,494 | 12/1969 | Walischmiller | 414/1 |
| 3,672,352 | 6/1972 | Summers | 128/665 |
| 3,888,362 | 6/1975 | Fletcher et al. | 901/16 |
| 4,005,782 | 2/1977 | Crockett | 901/16 |
| 4,024,959 | 5/1977 | Gruner | 901/16 |
| 4,058,001 | 11/1977 | Waxman | 128/660.07 |
| 4,089,293 | 5/1978 | Lyons | 901/16 |
| 4,150,326 | 4/1979 | Engelberger et al. | 318/563 |
| 4,355,645 | 10/1982 | Mitani et al. | 128/777 |
| 4,485,453 | 11/1984 | Taylor | 364/571 |
| 4,490,022 | 12/1984 | Reynolds | 351/211 |
| 4,571,750 | 2/1986 | Barry | 128/782 |
| 4,592,352 | 6/1986 | Patil | 606/130 |

(List continued on next page.)

FOREIGN PATENT DOCUMENTS

| | | |
|---|---|---|
| 664403 | 6/1963 | Canada . |
| 0326768 | 9/1989 | European Pat. Off. . |
| 3900976 | 7/1990 | Germany . |
| 59-157715 | 9/1984 | Japan . |
| 60-231208 | 11/1985 | Japan . |
| 603577 | 7/1976 | Russian Federation . |
| 2094590 | 9/1982 | United Kingdom . |

OTHER PUBLICATIONS

Science Accessories Corp. Advertisement, 2 pp. #SGP-2-3D-23.

"A New Device For Interactive, Image — Guided Surgery" by Galloway, Jr. et al. *Proceedings Of SPIG Conference On Medical Imaging*, 1991.

"An Articulated Neurosurgical Navigation System Using MRI and CT Images" by Kosugi et al., *IEEE Transactions On Biomedical Engineering*, vol. 35, No. 2, Feb. 1988.

(List continued on next page.)

*Primary Examiner*—William E. Kamm
*Attorney, Agent, or Firm*—Perman & Green, LLP

[57] ABSTRACT

The system and method includes a manipulator for manipulating a surgical instrument relative to a patient's body and, a position sensor for sensing the position of the surgical instrument relative to the patient's body. The manipulator can be manually or computer actuated and can have brakes to limit movement. In a preferred embodiment, orthogonal only motion between members of the manipulator is provided. The position sensor includes beacons connected to the patient and manipulator or surgical instrument and, a three dimensional beacon sensor adapted to sense the location and position of the beacons. Redundant joint sensors on the manipulator may also be provided. The system and method uses a computer to actively interact with the surgeon and can use various different input and output devices and modes.

9 Claims, 7 Drawing Sheets

U.S. PATENT DOCUMENTS

| | | | |
|---|---|---|---|
| 4,618,978 | 10/1986 | Cosman | 378/164 |
| 4,660,563 | 4/1987 | Lees | 128/654 |
| 4,665,928 | 5/1987 | Linial et al. | 128/782 |
| 4,691,694 | 9/1987 | Boyd et al. | 128/25 R |
| 4,750,487 | 6/1988 | Zanetti | 128/303 B |
| 4,755,642 | 7/1988 | Parks | 128/782 |
| 4,764,944 | 8/1988 | Finlayson | 378/20 |
| 4,766,465 | 8/1988 | Takahashi | 250/491.1 |
| 4,791,934 | 12/1988 | Brunnett | 128/653 |
| 4,846,173 | 7/1989 | Davidson | 606/130 |
| 4,945,914 | 8/1990 | Allen | 128/653 R |
| 4,979,949 | 12/1990 | Matsen, III et al. | 606/53 |
| 4,986,280 | 1/1991 | Marcus et al. | 128/782 |
| 4,986,281 | 1/1991 | Preves et al. | 128/782 |
| 5,024,236 | 6/1991 | Shapiro | 128/907 |
| 5,045,054 | 9/1991 | Hood et al. | 606/53 |
| 5,050,608 | 9/1991 | Watanabe et al. | 606/130 |
| 5,052,329 | 10/1991 | Bennett | 116/209 |
| 5,078,140 | 1/1992 | Kwoh | 606/130 |
| 5,090,401 | 2/1992 | Schwieker | 378/20 |
| 5,093,978 | 3/1992 | Binder | 901/16 |
| 5,100,411 | 3/1992 | Koutrouvelis | 606/130 |
| 5,112,340 | 5/1992 | Krenkel et al. | 606/130 |
| 5,119,817 | 6/1992 | Allen | 606/130 |
| 5,143,086 | 9/1992 | Duret et al. | 128/777 |
| 5,299,288 | 3/1994 | Glassman et al. | 606/130 |

OTHER PUBLICATIONS

"A Surgeon Robot Prostatectomies" by Davies et al., *Proceeding Of First International Workshop On Robotic Applications In Medicine And Health Care*, Jun. 23, 1988.

"Sterotaxical Microtelemanipulator For Ocular Surgery" by Guerrouad et al., *IEEE Engineering In Medicine & Biology Society 11th Annual International Conference*, 1989.

"Design Of A Surgeon — Machine Interface For Teleoperated Microsurgery" by Charles et al., *IEEE Engineering In Medicine & Biology Society 11th Annual International Conference*, 1989.

"The United Kingdom Advanced Medical Robotics Initiative" by Finlay, *IEEE Engineering In Medicine & Biology Society 11th Annual International Conference*, 1989.

"Force Feedback—Based Telemicromanipulation For Robot Surgery On Soft Tissues" by Sabatini et al., *IEEE Engineering In Medicine & Biology Society 11th Annual International Conference*, 1989.

"Advanced Interfaces For Teleoperated Biomedical Robots" by Bergamasco et al., *IEEE Engineering In Medicine & Biology Society 11th Annual International Conference*, 1989.

"A Model–Based Graphics Interface For Controlling A Semi–Autonomous Mobile Robot" by Regalbuto et al., *IEEE Engineering In Medicine & Biology Society 11th Annual International Conference*.

"Robot Total Hip Replacement Surgery In Dogs" by Taylor et al., *IEEE Engineering In Medicine & Biology Society 11th Annual International Conference*.

"Watchdog Safety Computer Design And Implementation" by Kilman et al., *RI/SME Robots 8 Conference*, Jun. 1984.

"Development and Initial Clinical Evaluation of Pre–Robotic and Robotic Retracton Systems For Surgery" by McEwen et al., *Proceeding Of Second Workshop On Medical And Health Care Robotics*, IARP, Newcastle, OK, Sep. 5–7, 1989 and *IEEE Engineering In Medicine And Biology Society 11th Annual International Conference*, 1989.

Klinger Catalog 90, p. 108, 1990.

SYSTEM FOR MANIPULATING MOVEMENT OF A SURGICAL INSTRUMENT WITH COMPUTER CONTROLLED BRAKE

This is a divisional of application Ser. No. 08/147,008 filed Nov. 2, 1993, which is a continuation of application Ser. No. 07/714,816 filed Jun. 13, 1991; abandoned.

BACKGROUND OF THE INVENTION

1. Field of the Invention

The present invention relates to surgery and, more particularly, to a system and method for positioning, moving and locating surgical instruments for performing surgery on a patient.

2. Prior Art

Recent advances in medical imagining technology (CT, MRI, PET, etc.), coupled with advances in computer-based image processing and modelling capabilities have given physicians an unprecedented ability to visualize anatomical structures in live patients, and to use this information in diagnosis and treatment planning. The precision of image-based pre-surgical planning often greatly exceeds the precision of actual surgical execution. Precise surgical execution has been limited to procedures, such as brain biopsies, in which a suitable sterotactic frame is available. The inconvenience and restricted applicability of such a frame or device has led many researchers to explore the use of robotic devices to augment a surgeon's ability to perform geometrically precise tasks planned from computed tomography (CT) or other image data. The ultimate goal of this research is partnership between a man (the surgeon) and machines (computers and robots), that seeks to exploit the capabilities of both, to do a task better than either can do alone. Machines are very precise and untiring and can be equipped with any number of sensory feedback devices. Numerically controlled robots can move a surgical instrument through an exactly defined trajectory with precisely controlled forces. On the other hand, the surgeon is very dexterous. He is also quite strong, fast, and is highly trained to exploit a variety of tactile, visual, and other cues. "Judgementally" controlled, the surgeon understands what is going on in the surgery and uses his dexterity, senses, and experience to execute the procedure. However, the surgeon usually wants to be in control of everything that goes on. If the surgeon desires to increase precision within acceptable limits of time or with sufficient speed, he must be willing to rely on machines to provide the precision.

One potential problem with a robotic device is undesired motion. The most obvious way to prevent a robotic device from making an undesired motion is to make it incapable of moving of its own accord. Motor-less manipulators have been implemented in the past which use joint encoders to provide feedback to the surgeon on where his instruments are relative to his image-based surgical plan. European Patent Application 326,768A2 describes one such device. One important limitation of this approach is that it is often very difficult for a person to align a tool accurately in six degrees-of-freedom with only the use of positional feedback. Passive manipulators, permitting free motion until locked, have also been implemented in the past for limb positioning, tissue retraction, instrument holding, and other applications in which accuracy is not important. A three degree-of-freedom passive manipulation aid for prostate surgery has also been used clinically in the past.

In cases where only a single motion axis is required during the "in contact" phase of the surgery, a robot has been used in the past essentially as a motorized sterotactic frame. A passive tool guide is placed at the desired position and orientation relative to the patient. Brakes are applied and robot power is turned off before any instrument touches the patient. The surgeon provides whatever motive force is needed for the surgical instruments themselves and relies on his own tactile senses for further feedback in performing the operation. This approach ameliorates, but does not entirely eliminate, the safety issue raised by the presence of an actively powered robot in close proximity to to the patient and operating room personnel. Furthermore, maintaining accurate positioning is not always easy, since many robots tend to "sag" a bit when they are turned off or to "jump" when brakes are applied. Leaving power turned on and relying on the robot's servocontroller to maintain position introduces further safety exposures. Finally, this type of approach is limited to cases where a fixed passive guide suffices. The surgeon cannot execute a complex pre-computed trajectory by use of this approach, nor can he precisely relocate an instrument or body part from one place to another.

Over the past several years, researchers at IBM and the University of California at Davis developed an image-directed robotic system to augment the performance of human surgeons in precise bone machining procedures in orthopedic surgery, with cementless total hip replacement surgery as an initial application. This application inherently requires computer controlled motion of the robot's end-effector while it is in contact with the patient. Thus, considerable attention had to be paid to safety checking mechanisms. In-vitro experiments conducted with this system demonstrated an order of-magnitude improvement in implant fit and placement accuracy, compared to standard manual preparation techniques. A clinical trial on dogs needing hip replacement operations is presently underway.

It is the objective of the present invention to provide a new and improved system and method for augmentation of surgery.

SUMMARY OF THE INVENTION

The foregoing problems are overcome and other advantages are provided by a new and improved system and method for augmentation of surgery.

In accordance with one embodiment of the present invention, an apparatus for use in moving an end effector is provided. The apparatus comprises a first manipulator and a second manipulator. The first manipulator comprises a coarse motion manipulator and a fine motion manipulator. The second manipulator is connected to a distal end of the first manipulator. The second manipulator has means for providing orthogonally decoupled degrees of freedom with a common remote center-of-motion located at a work point some distance from the manipulator mechanism, means for selectively locking or releasing the separate degrees of freedom, and arranged so that small rotational realignments of an end effector connected to the end of the second manipulator can be provided without requiring large motions of any manipulator joint. This mechanism provides at least three orthogonally decoupled revolute degrees of freedom, together with additional linear degrees of freedom.

In accordance with another embodiment of the present invention, a system for manipulating movement of a surgical instrument is provided. The system comprises a mechanical positioner, a computer controlled brake, a computer, and means for signaling the computer. The mechanical positioner is adapted to have the surgical instrument connected thereto and comprises a plurality of members connected to each other in a series with at least one motion joint between two of the members. The computer controlled brake is located at the motion joint. The computer is connected to the brake for selectively actuating the brake upon an occurrence of a predetermined event. The means for signaling the computer can signal the computer of the occurrence of the predetermined event.

In accordance with another embodiment of the present invention, a system for assisting the surgeon in positioning a surgical instrument relative to a target position is provided. The position of a surgical instrument, means for sensing the position of the surgical instrument, means for determining a path from a sensed position of the surgical instrument to the target position, and means for audibly signaling deviation of the position of the surgical instrument from the path.

In accordance with another embodiment of the present invention, a system for assisting a surgeon in positioning an article relative to a target position is provided. The system comprising means for determining a surgical plan based upon input patient information, means for sensing surgical execution of the surgical plan by the surgeon, means for advising the surgeon and means for automatically selecting different types of advice. The means for advising the surgeon can advise the surgeon based upon comparison of the surgical plan and the sensed surgical execution. The means for automatically selecting different types of advice can select different types of advice to give the surgeon based upon the surgical plan and the sensed surgical execution.

In accordance with another embodiment of, the present invention, a system for assisting a surgeon during surgery is provided. The system comprises means for determining a surgical plan based upon input patient information, means for sensing surgical execution of the surgical plan by the surgeon, means for advising the surgeon, and means for inputting a change in the surgical plan. The means for advising the surgeon can advise the surgeon of the surgical plan and the sensed surgical execution during the surgery. The means for advising comprises a computer. The means for inputting a change in the surgical plan can input a change in the surgical plan into the computer during surgery and determine a new surgical plan based, at least partially, upon previously sensed surgical execution of the surgical plan.

In accordance with another embodiment of the present invention, an apparatus for moving a surgical instrument relative to a patient is provided. The apparatus comprises a base, a first link, a second link, a third link, a fine adjustment manipulator, and means for selectively locking and unlocking movement. The first link is movably mounted to the base for movement along a first axis of motion. The second link is movably mounted to the first link for movement along a second axis of motion perpendicular to the first axis of motion. The third link is movably mounted to the second link for movement along a third axis of motion perpendicular to the first and second axes of motion. The fine adjustment manipulator comprises a first section movably mounted to the third link along a fourth axis of motion. The fine adjustment manipulator also comprises a second section movably mounted to the first section along a fifth axis of motion perpendicular to the fourth axes of motion, and a third section movably mounted to the second section along a sixth axis of motion perpendicular to the fourth and fifth axes of motion. The means for selectively locking and unlocking can lock and unlock movement of individual links and sections to provide orthogonal only movement between connected links and sections upon unlocking of the links and sections.

In accordance with another embodiment of the present invention, a signaling device for use with a position monitoring system for use in a surgical operation is provided. The device comprises a pin, and a beacon. The pin has a center axis and is adapted to be positioned into a patient's body. The beacon has a housing and an energy emitter. The housing has a channel adapted to receive an end of the pin therein, a channel axis coaxial with the energy emitter, and means for positioning the housing at a predetermined position on the pin such that the energy emitter is coaxially aligned with the center axis of the pin when connected thereto.

In accordance with another embodiment of the present invention, a system for assisting a surgeon during surgery is provided. The system comprises means for sensing a surgical operation, and means for automatically selecting different sensing modes. The means for sensing includes different modes of sensing. The means for automatically selecting different sensing modes can select the different sensing modes based upon the sensed surgical operation or on the sensed progress of the surgical operation relative to a predefined surgical plan.

In accordance with one method of the present invention, a method of assisting a surgeon in positioning a surgical instrument relative to a patient's body during surgery comprises steps of connecting beacons to the patient; providing a passive manipulator for moving the surgical instrument; connecting the surgical instrument to the manipulator; connecting beacons to the manipulator; determining the positions of the beacons on the patient relative to a portion of the patient's body; and sensing movement of the beacons on the manipulator relative to the beacons on the patient and thus, sensing the movement of the manipulator relative to the portion of the patient's body.

In accordance with another method of the present invention a method of sensing relative positioning of multiple portions of a patient's body during surgery is provided. The method comprises steps of connecting beacons to portions of the patient's body; measuring the locations of the beacons; sensing the position of reference points on the patient's body; determining the position of the beacons relative to the sensed reference points; tracking the movement of the beacons; and determining the positions of the portions of the patient's body relative to each other based upon the relative movement of the beacons to each other.

In accordance with another embodiment of the present invention, an apparatus for assisting a surgeon in manipulating a surgical instrument intended to be placed into a patient's body through an opening in which there is a relatively small amount of lateral motion at the opening is provided. The apparatus comprises a first manipulator; and a second manipulator. The second manipulator is connected to the first manipulator and comprises at least three orthogonally decoupled revolute degrees of freedom and is positionable relative to the opening to provide a center of motion at the opening, and means for connecting the surgical instrument to the second manipulator. The means for connecting may include a sliding link for axially sliding the surgical instrument to provide an apparatus that provides a spherical work volume centered at the opening.

In accordance with another method of the present invention, a method of tracking position of a surgical instrument inside a patient's body is provided comprising steps of inserting a first surgical instrument into a patient's body, the first instrument having a visual target thereon; inserting a second surgical instrument into the patient's body, the second instrument having means for transmitting an image out of the patient's body; and moving at least one of the surgical instruments automatically based upon the movement of the other surgical instrument such that the visual target can be substantially constantly transmitted by the means for transmitting an image.

DETAILED DESCRIPTION OF THE DRAWINGS

The foregoing aspects and other features of the invention are explained in the following description, taken in connection with the accompanying drawings, wherein.

DETAILED DESCRIPTION OF THE INVENTION

Figure 1A:
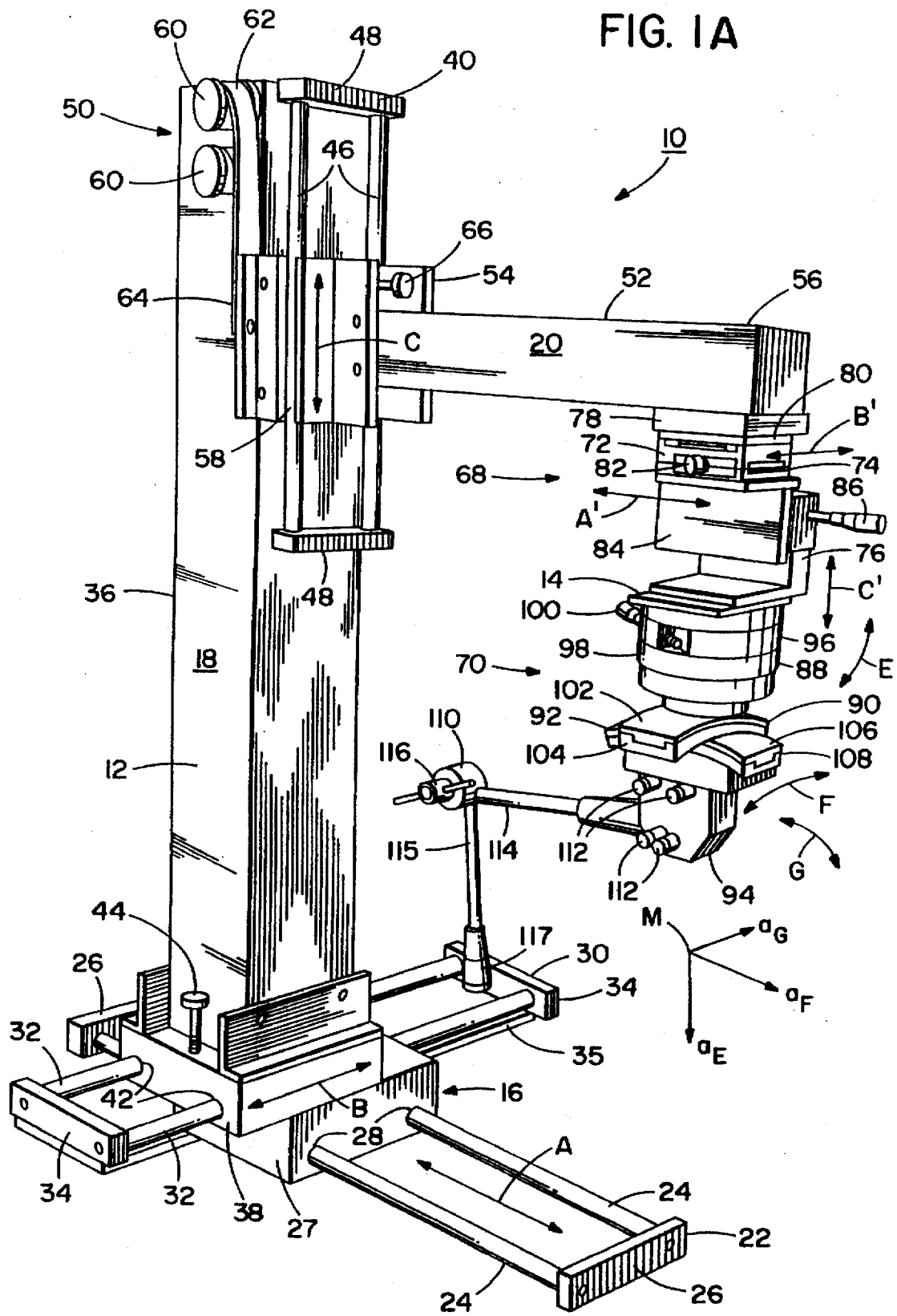
FIG. 1A is a schematic perspective view of a positioning apparatus incorporating features of the present invention.

Referring to FIG. 1A, there is shown a schematic perspective view of a positioning apparatus 10 incorporating features of the present invention. Although the present invention will be described with reference to the embodiments shown in the drawings, it should be understood that the present invention is capable of being used in various different types of embodiments and methods. In addition, any suitable size, shape, or type of elements or materials can be used. As used herein, the terms "position" or "positioning" is intended to mean location and/or orientation. Also as used herein, the term "orthogonally decoupled" is intended to mean that small individual motions of manipulator joints affect only single, orthogonal degrees of freedom of the manipulator's end effector or of an object held in the manipulator's end effector. Thus, individual joints may be used easily, intuitively, and independently to align degrees of freedom of the end-effector to achieve a desired goal. Two linear degrees of freedom are orthogonal if they are perpendicular. Similarly, two revolute degrees of freedom are orthogonal if the directions of their axes of rotation are perpendicular. Further, a revolute degree of freedom about a line axis is orthogonally decoupled from linear degrees of freedom resolved at a point M if the line axis "a" passes through the point M. The mechanisms described herein provide orthogonally decoupled motion resolved at a point located some distance from the mechanical structure. Typically, they comprise, serially, a mechanism providing three orthogonally decoupled linear motions, followed by a remote center-of-motion "wrist" providing orthogonally decoupled revolute motions, followed by an adjustable tool holding mechanism permitting a desired tool or body part to be placed at a desired position and orientation relative to the wrist center of motion. Typically, the successive axes-of-rotation of the wrist are perpendicular and intersect at the center of motion, so that any rotation about any wrist axis introduces no translational displacement of a tool or body part held at the center of rotation. Furthermore, the wrist is arranged so that any desired small reorientation of the tool or body part held at the center-of-rotation may be accomplished with only small angular motions about the individual wrist axes. In many cases, the mechanisms described herein comprise kinematically redundant instances of linear and rotational sub-mechanisms to support a variety of coarse-fine manipulation methods.

The positioning apparatus 10, in the embodiment shown, generally comprises a bulk or coarse motion manipulator 12 and a fine motion manipulator 14. The apparatus 10 is generally intended to be used in an operating room. A similar system is disclosed in copending U.S. patent application Ser. No. 07/523,611 filed May 11, 1990 entitled "Image-Directed Robotic System For Precise Robotic Surgery Including Redundant Consistency Checking" assigned now U.S. Pat. No. 5,086,401 to the same assignee as herein which is hereby incorporated by reference in its entirety herein. The coarse motion manipulator 12 generally comprises three links or sections; first link 16, second link 18, and third link 20. In the embodiment shown, the first link 16 is movably mounted on a base having a rail system 22. In a preferred embodiment, the base 22 would be stationarily positioned on a floor of an operating room to stationarily position the positioning apparatus 10 during a surgical operation. Alternatively, the base 22 could be fixed to an operating table. In the embodiment shown, the base 22 comprises two rails 24 and two end blocks 26 at opposite ends of the rails 24. The first link 16 has a main block 27 with rail channels 28 that the rails 24 pass through such that the first link 16 can ride along the base 22 along a linear path or axis as shown by arrow A. A suitable manual position lock (not shown) is provided on the block 27 to selectively stationarily position or lock the first link at a selected position on the base 22. The end blocks 26 establish a limited range of motion for the first link 16 on the base. The first link 16 also comprises a second rail system 30 stationarily connected to the block 27. The second rail system 30 generally comprises two rails 32, two end blocks 34, and beam 35 that connects the rail system to the block 27. As can be seen in FIG. 1A, the second rail system 30 is generally perpendicular to the first rail system 22 and moves with the block 27 as it moves along the first rail system 22.

Figure 1B:
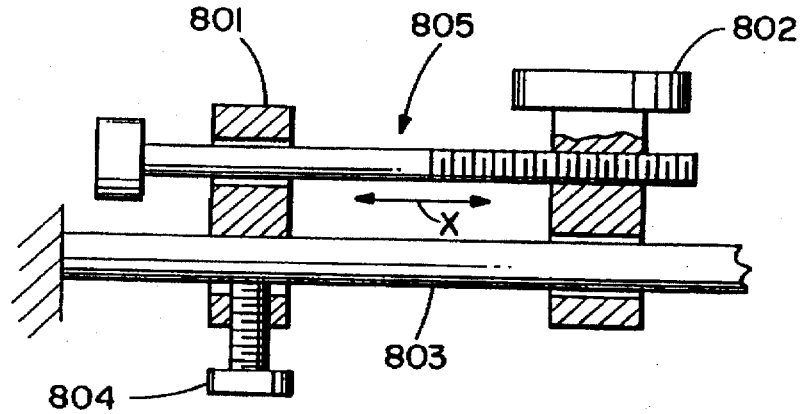
FIG. 1B is a schematic view of a lock or brake with a micrometer adjuster.

Although the apparatus 10 shown in FIG. 1A is being described as a manual passive movement apparatus, it should be understood that any manual locks described could be replaced by a computer controlled brake. This computer controlled brake can be either a simple binary lock or may provide a variable, controlled braking force. Furthermore, it should be made clear that any lock controlling a single degree-of-freedom could be augmented by a suitable lock with auxiliary micrometer adjustment permitting fine positional adjustment after the lock is applied. It should be understood that "micrometer adjustment" may comprise any suitable type of very precise fine motion adjustment device, and is not limited to a fine pitch lead screw, such as is commonly found on commercial micrometer stages. Micrometer adjustment can be provided at any joint, either in the coarse or fine manipulators, and may be either manually controlled or computer controlled, or both. Finally, it should be made clear that such micrometer adjustments can be manually or computer activated and controlled. One typical mechanism is illustrated schematically in FIG. 1b, although other implementations are possible. In this schematic, moving members 801 and 802 are constrained by appropriate bearing structures so that they move in only a single degree of freedom X relative to fixed member 803. Locking mechanism 804 locks moving member 801 to fixed member 803. Micrometer lead screw 805 provides a means of adjusting the relative displacement along degree-of-freedom X of moving member 802 relative to moving member 801. Thus, when moving member 801 is locked relative to fixed member 803, micrometer lead screw 805 can be used to adjust the position of moving member 802 relative to fixed member 803.

The second link 18, in the embodiment shown, generally comprises a column shaped frame 36 with a bottom end movement block 38 and a top end third rail system 40. The bottom end movement block 38 has rail channels 42 through which the second rail system rails 32 project through. This system allows the bottom end movement block 38, and thus the second link 18, to move along the second rail system 30 in the linear path or axis as shown by arrow B. As can be seen, the linear path of the second link 18 is orthogonal to the linear path of the first link 16 as shown with arrow A. The end blocks 34 allow the second link 18 to have a limited range of movement on the second rail system 30. The bottom end movement block 38 also comprises a manually actuatable lock 44 to enable the user to selectively lock the relative position of the second link 18 to the first link 16. The top end third rail system 40 is similar to the first and second rail systems and generally comprises two rails 46 and two end blocks 48 which are stationarily connected to the second link frame 36. The second link 18, in the embodiment shown, also includes a counter balance system 50 which will be further described below.

The third link 20, in the embodiment shown, generally comprises a frame 52, a movement block 54 at a first end proximate the second link 18, and a distal end 56. The movement block 54, in the embodiment shown, has rail channels 58 which the rails 46 pass through. The movement block 54 is slidably positioned on the rails 46 for movement in the vertical direction as shown by arrow C with the end blocks 48 providing a limit to the range of motion of the third link 20. Due to the forces of gravity, the counterbalance system 50 is provided to counter balance the effects of gravity on the third link 20, thus making the third link 20 substantially easier for a surgeon to move. The counterbalance system 50, in the embodiment shown, generally comprises dowels 60 stationarily connected to the frame 36 of the second link and constant force springs 62. First ends 64 of the springs 62 are fixedly connected to the movement block 54. The remainder of the springs 62 are coiled around the dowels 60 and have an undeformed coil shape. As the third link 20 is moved from the top of the third rail system 40 towards the bottom of the third rail system. The movement block 54 pulls on the first ends 64 of the springs 62 and pulls the springs 62 out from the dowels 60 causing the springs 62 to deform into a relatively straight shape. The resistance of the springs 62 to deformation counterbalances the weight of the third arm 20 and the apparatus attached to its distal end 56. The movement block 54 also comprises a manually actuatable lock 66 which can be used by the surgeon to selectively lock the position of the third link 20 relative to the second link 18.

The coarse motion manipulator 12 as described above is generally intended to be used as a passive manipulator for moving the fine motion manipulator 14 and surgical instrument connected thereto. Thus, the surgeon can move each one of the links, either successively or together, to roughly or generally position a surgical instrument. The locks at the joints between the links can be used to prevent relative motion between the links. These locks can be actuated either successively or together. It should be understood that any suitable type of relative motion system could be used between the links; not merely rail systems. The links could also be pivotally connected to each other. However, in a preferred embodiment the three links are capable of orthogonal only motion relative to each other. This orthogonal only motion or degrees-of-freedom assists the surgeon in positioning or moving the coarse motion manipulator 12 due to the restricted path of motion available to each link. Thus, the surgeon can easily foresee the effect on the fine motion manipulator 14 if one of the links of the coarse motion manipulator is moved. In a system where computer controlled locks or brakes are provided with the apparatus 10, one embodiment of such a computer-controlled position lock would be an electric particle brake operating through a rack-and-pinion transmission mechanism. Such an embodiment permits the computer to control the braking force from zero or very low drag up to full locking. Such variable braking force can be used both to provide additional tactile feedback to the surgeon and to provide additional damping to assist him in positioning the mechanism. If desired, additional manually actuated position locks may be provided with the computer-actuated position locks.

The fine motion manipulator 14, in the embodiment shown, generally comprises a linear motion section 68 and a rotational manipulator section 70. The linear motion section 68, in the embodiment shown, generally comprises three sections; a first section 72, a second section 74, and a third section 76. A mounting block 78 is provided at the distal end 56 of the third link 20 for mounting the fine motion manipulator 14 to the coarse motion manipulator 12. In the embodiment shown, stationarily connected to the mounting block 78 is a race member 80. Movably mounted to the race member 80 is the first section 72. The first section 72 can move relative to the race member 80 in a linear path or axis as shown by arrow B'. This linear path B' is parallel to the path B of the second arm 18, but substantially smaller in allowable travel path length. The actual mechanical connection between the first section 72 and race member 80 is provided by the top of the first section 72 having an interlocking engagement with the race member 80 to prevent movement in all directions except along path B'. Suitable roller bearings are provided in the joint between first section 72 and race member 80 to provide relatively smooth motion. In the embodiment shown, the connection of the first section 72 to the race member 80 also comprises a lock (not shown) which can be selectively manually actuated by a surgeon to lock or fix the relative positions thereof.

The bottom of the first section 72 has the top of the second section 74 movably connected thereto such that the second section 74 can move relative to the first section 72. The bottom of the first section 72 has a linear raceway. The top of the second section 74 also has a linear raceway that interlocks with the first section bottom raceway to prevent movement in all directions except along path A'. Suitable roller bearings or the like and stops or ledges are provided between the first and second sections to provide a smooth movement. A lock 82 is provided at the joint between the first and second sections such that a surgeon can selectively manually lock the two sections to each other. The movable path of the second section 74 as shown by arrow A' is orthogonal to the movement path of the first section 72 as shown by arrow B' and, is parallel to but substantially smaller than the path length of the first arm 16 shown by arrow A. The bottom of the second section 74 has a frame structure 84 fixedly connected thereto. A side of the frame structure 84 has the third section 76 movably mounted thereon for movement along a substantially vertical path or axis as shown by arrow C'. The path of the third section 76 parallel to, but substantially less than the path C of the third arm 20 on the second arm 18. The side of the frame structure 84 has a linear raceway thereon that interlocks with a linear raceway on the third section 76 to prevent movement in all directions except along path C'. A zero-force spring counterbalance mechanism (not shown) similar to counterbalance mechanism 50 is provided at the third section 76 which compensates for the weight of the entire mechanism distal to frame structure 84. Suitable rollers are provided between third section 76 and frame structure 84 for a smooth motion. In the embodiment shown, a manual lock 86 is provided at the joint of the third section 76 and frame structure 84 to control relative movement therebetween. Additionally, a manually actuatable micrometer adjuster could be provided at the joint. The first and second sections 72 and 74 could also include micrometers at their joints. The third section 76, in the embodiment shown, has a general "L" shape with a bottom having the rotational manipulator section 70 connected thereto. Thus, when any of the sections 72, 74 or 76 are moved, the rotational manipulator section 70 is moved.

One of the features of the present invention is the orthogonal only redundant linear motion system provided by the coarse motion manipulator 12 and fine linear motion section 68. The orthogonal only motion of the sections 72, 74 and 76, similar to the orthogonal only motion of the coarse motion manipulator 12, assists the surgeon in manipulation of the fine linear motion section 68 due to the restricted path of motion available to each section. Thus, the surgeon can easily foresee the effect if one of the sections is proposed to be moved and, control of movement is simplified. Although redundant linear motion is described above, it should be understood that this need not be provided. A rotational coarse motion manipulator may be provided between manipulator 12 and manipulator 14. This, of course, would be more useful to align the fine motion axes so that they are conveniently located for a particular manipulation task.

Also similar to the coarse motion manipulator 12, the fine linear motion section 68 is generally intended to be used as a passive manipulator for moving the rotational manipulator section 70. The surgeon can move each one of the sections either successively or together to finely position the section 70 after having been moved by the coarse motion manipulator 12. This redundant motion system can allow a surgeon to move a surgical instrument into position much faster than a single motion system and with good accuracy due to fast motion provided by the coarse motion manipulator 12 and the accurate motion provided by the fine linear motion section 68. The accuracy provided by the fine linear motion section 68 allows the coarse motion manipulator 12 to be moved faster because of the decrease in accuracy needed to position the coarse motion manipulator 12. Another advantage of the coarse/fine structure is that it permits relatively large work volumes while limiting the inertia that the surgeon must cope with. The modularity is similarly very useful for experimentation.

The rotational manipulator section 70, in the embodiment shown, generally comprises a roll section 88, a pitch section 90, a yaw section 92, and an end section 94. The roll section 88 generally includes two race plates 96 and 98 that are movably connected to each other to provide rotation about the vertical axis as shown by arrow E. The top plate 96 is fixedly connected to the third section 76. A suitable manual or computer controllable lock is provided to fix or lock the two plates 96 and 98 together. In the embodiment shown, the locking mechanism contains a micrometer adjustment mechanism 100 to provide extremely fine adjustments of the angle between plates 96 and 98 after the lock is applied. The pitch section 90 is a goniometer cradle which has two curved plates 102 and 104 movably connected to each other. The top plate 102 is fixedly connected to the roll section bottom plate 98. The bottom plate 104 is adapted to move along a curved or revolute path relative to the top plate 102 as shown by arrow F. The yaw section 92 is a goniometer cradle which includes two curved plates 106 and 108 that are movably connected to each other. The top plate 106 is fixedly connected to the pitch section bottom plate 104. The bottom plate 108 is adapted to move in a curved or revolute path relative to the top plate 106 as shown by arrow G. The individual rotational manipulator sections, in the embodiment shown, are each limited to motion in their receptive relative paths of motion E, F and G. The axes of rotation of the paths E and F are perpendicular, as are the axes of rotation of the paths F and G.

Furthermore, the axis of path E is perpendicular to axis of path G when pitch section 92 is in its normal center of motion. All three axes $a_E$, $a_F$, and $a_G$ of paths E, F, and G intersect at a motion center point M at a convenient distance from the fine manipulator mechanism. Thus, the rotational manipulator section 70 provides orthogonally decoupled rotational motions resolved at this motion center point. Further, the rotational motions resolved at this point are orthogonally decoupled from the translational motions of the more proximal translational sections (i.e., coarse motion section 12 and fine linear motion section 68). Suitable manual actuated locks are provided at each section to provide selective movement. Alternatively or additionally, micrometers can be provided at each section. In addition, single additional redundant sections could be provided.

As noted above, suitable locks are provided at each section to provide selective motion. It should also be understood that automatic computer actuated locks and/or manual locks could be provided in both the coarse and fine motion manipulators. One embodiment of such a computer-controlled position lock could be an electric particle brake operating through a rack-and-pinion transmission mechanism. Such an embodiment would permit the computer to control the braking force from zero or very low drag up to full locking. Such variable braking force can be used both to provide additional tactile feedback to the surgeon and to provide additional damping to assist him in positioning the mechanism. If desired, both manually actuated and computer actuated position locks or brakes may be provided.

It will thus be seen that the embodiment shown supports a coarse-fine manipulation strategy. In this strategy, the coarse manipulator 12 is positioned so that the remote center-of-motion of the fine manipulator 14 is located at a desired position and the motion axes A' and B' (or A', B', and C' if an alternative embodiment such as a ball-and-socket joint is substituted for revolute joint between manipulators 12 and 14 are aligned conveniently for the surgeon). The coarse manipulator 12 is then locked, and the fine manipulator 14 is adjusted so that axes $a_E$, $a_F$, and $a_G$ of the revolute paths E, F, and G are aligned conveniently and are mutually orthogonal. Finally, the joints at the revolute paths E, F, and G and the linear paths A', B', and C' are used to perform the desired fine positioning or realignment motions. These jointts may be selectively locked or freed as necessary to assist in carrying out the desired motions. Because the fine motions are orthogonally decoupled, readjustment of one degree-of-freedom will not affect the alignment of other degrees-of-freedom, thus significantly speeding up the process of achieving a desired alignment. Furthermore, the process is relatively insensitive to small errors in the placement of the coarse manipulator, unless large rotational adjustments are to be made. For example, suppose there is an error of 0.5 mm in the placement of the coarse manipulator relative to a desired center of motion. Then, a rotational realignment of 15° will produce only about 0.13 mm undesired motion of the rotation center, which is often negligible or which may easily be compensated by fine adjustments of linear motion axes A', B', and C'. A related advantage of the bulk/fine structure is that is permits relatively large work volumes while limiting the inertia that the surgeon must cope with. The modularity is similarly very useful for experimentation.

In the embodiment shown, the end section 94 is fixedly connected to the bottom plate 108 of the yaw section 92 and includes means for mounting the extension tool 110 thereon and, beacons 112. The extension tool 110 is known in the surgical art. The tool 110 has two arms 114 and 115 with a center clamp control 116 that is adapted to fix the two arms relative to each other and, clamps at the ends of the arms 114 and 115 also controlled by the control 116. The clamp at the end of the first arm 114, in the embodiment shown, fixedly clamps onto the end member 94. The clamp 117 at the second arm 115 is adapted to clamp onto a surgical instrument (not shown). In normal use, the tool 110 can be adjusted such that a desired point on the surgical instrument or a desired point on a body part held on the surgical instrument is located at the center of motion M of the manipulator 70. However, the tool 110 need not be used. A surgical instrument may be directly connected to the end section 94 or, any suitable intermediate mechanism may be provided. The beacons 112, in the embodiment shown, are generally comprised of light emitting diodes. However, any suitable type of energy emitters or reflectors may be used. The diodes 112 are used to signal the position, both orientation and location, of the end section 94.

Suitable calibration procedures may be used to determine the position of the remote center-of-motion of the revolute manipulator section 70 relative to the beacons. In one such procedure, all joints proximal to the manipulator section 70 are locked. The joints of the revolute manipulator section 70 are then all moved to multiple positions and the positions of the beacons are measured by sensor 122 (described below). Each beacon will move about on the surface of a sphere whose center coincides with the remote center-of-motion of the revolute manipulator section 70, although the radius of each beacon's sphere-of-motion may differ from that of another beacon's sphere-of-motion. Standard mathematical techniques may be used to compute this common center from the measured beacon positions.

Figure 2:
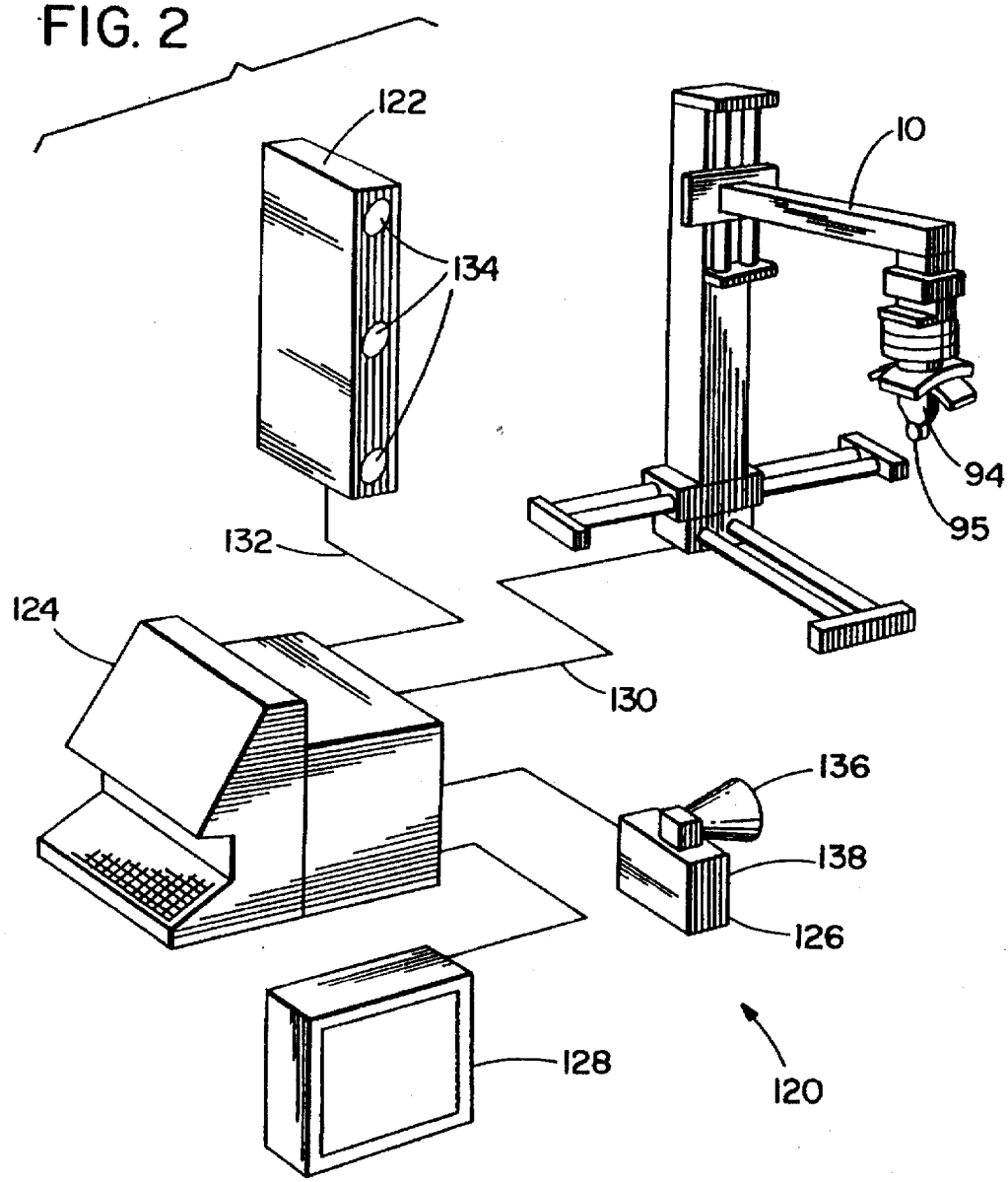
FIG. 2 is a schematic view of a system incorporating features of the present invention having the positioning apparatus shown in FIG. 1.

Referring also to FIG. 2, there is shown one embodiment of a system 120 incorporating the apparatus 10 shown in FIG. 1. The system 120 generally comprises the apparatus 10, a sensor 122, a computer 124, an audio system 126, and a visual display 128. The beacons 112 (see FIG. 1) on the end section 94 are connected to the computer 124 by electrical cable 130. The computer 124 sends signals to the beacons 112 such that they are activated in predetermined patterns of time and frequency. In an alternate embodiment different beacon colors could be used to distinguish the beacons from each other, thus permitting all beacon positions to be measured simultaneously. The sensor 122, in the embodiment shown, is an optical sensor that can digitize optical information and transmit the information via cable 132 to the computer 124. In a preferred embodiment, the sensor 122 is an OPTOTRAK 3D digitizer. OPTOTRAK is a trademark of Northern Digital Corporation. The sensor 122 uses three CCD linescan cameras 134 to track the active LED beacons. This system is fast, accurate, much less readily confused by stray light than similar lateral-cell based devices, and unlike electromagnetic field 6D sensors, is unaffected by metal in the operating theatre. The sensor 122 has been found capable of producing 1000 3D positions per second to an accuracy of about ±0.1 mm and of returning up to eight 6D positions with an additional time of about 10 ms beyond the 3D sampling time. The computer 124, in the embodiment shown, can calculate the positions of the end section 94 based upon the light from the beacons 112 sensed at the sensor 122. The audio system 126 is connected to the computer 124 and has a speaker 136 and an input 138 for use with a voice recognition system in the computer. The speaker 136 may be used to output computer-generated synthetic speech, prerecorded voice messages, or simple tonal or other audio cues. However, the audio system 126 need not be provided. The visual display 128 is connected to the computer 124 and is used to display information to the surgeons. The display 128 can be located in any suitable location in the operation room.

The system 120, in the embodiment shown, is generally capable of sensing the position, both location and orientation, of the end section 94. In one embodiment, the position of the surgical instrument relative to the end section 94 is input into the computer 124 prior to use of the surgical instrument. The computer 124 is thus capable of determining or calculating the position, both location and orientation, of the surgical instrument when it is moved. In an alternate embodiment, beacons are alternatively or additionally connected directly to the surgical instrument. Thus, in this alternative embodiment, the sensor 122 is capable of directly sensing the position of the surgical instrument when it is moved. The system can also be used to keep track of all of the surgical instruments used in an operation to insure that all instruments are properly recovered. The system can obviously be used for a variety of purposes, but one of the significant advantages of the system is as a means for determining the relative position of a surgical instrument relative to the patient and, as a means for determining the relative position of a portion of the patient's anatomy relative to another portion of the patient's anatomy or a target area. For this purpose, beacons can be directly connected to the patient or portions of the patient's anatomy as further described below. Unlike the mechanical computer-aided surgery apparatus in the prior art, such as disclosed in European Patent Application 326768A2, the optical system described above provides a much less cumbersome system adapted for use in a multitude of different applications.

A preferred system architecture for the present invention can be generally described as two subsystems or groups; a presurgical modeling and planning system and method, and the surgical system substantially as described above and below. The presurgical system and method generally uses models of patient information to assist the surgeon in planning precise surgical procedures. Any suitable type of presurgical system and method could be used. In one type of presurgical procedure, described below for informational purposes only, the principal components of this presurgical procedure include a medical image database and display system, an anatomical model builder, an anatomical feature extractor, a surgical simulator, an anatomical data base, and a surgical plan optimizer. These components are used to produce a surgical plan. The medical image database and display system supports archival, retrieval, low-level processing, and display of CT, MRI, and other images. The anatomical model builder transforms recorded images into 3D solid models of the patient's anatomy. The process proceeds in three steps. In the first step (segmentation), each voxel in the CT data set is assigned a tissue classification label, based on an adaptive thresholding technique. In the second step (model reconstruction), a winged-edge boundary representation of each connected set of tissue classified as "bone" is constructed by a variation of Baker's "weaving wall" algorithm. In the third step (model simplification), coplanar faces are merged to reduce the size of the model somewhat. The anatomical feature extractor identifies anatomical features from the models. These features include standard morphometric landmarks, ridge curves, and surface patches bounded by ridge curves and geodesics between landmarks. The present implementation is semi-automatic. A technician "seeds" the search by identifying points on or near ridge curves, and the computer then locates and follows the ridge curves. A more automatic procedure may of course be used. The surgical simulator permits a surgeon to interactively specify where he wishes to cut the bones apart and to manipulate the pieces graphically. It also permits him to display the bone fragment motions computed by the plan optimizer (described below) and to modify the plan as he chooses. The anatomical data base summarizes anatomical feature information for "normal" individuals. The surgical plan optimizer uses information from the anatomical data base to compute optimal motions of each bone fragment to most closely approximate the corresponding anatomy of a "normal" individual of the same age, race, sex, and size as the patient. The surgical plan produced consists of the model data, the location and sequence of the cuts, the location of key anatomical features to be used in registering the patient to the model data and the planned optimal motion of each bone fragment.

The surgical system and method preferably includes a surgeon interface system and passive manipulation aids. The surgeon interface uses a variety of modalities such as graphics, synthesized voice, tonal cues, programmable impedance of manipulator joints, etc., to provide online, realtime "advice" to the surgeon, based on the sensed relationship between the surgical plan and surgical execution. A quite sophisticated, "intelligent" system can be used that uses its model of the surgical plan to automatically customize displays, select appropriate sensor tracking modes, and help interpret inputs from the surgeon. In this ultimate system, a helmet-mounted sterographic display could be used to project the surgical advice directly onto the surgeon's visual field, and the surgeon could use voice input to tell the system what he wants. In a basic system, very simple realtime graphics and auditory cues can be provided for alignment. For use with bone fragments, an online 3D model display can provide somewhat more detailed "snapshots" of bone fragment positions relative to the surgical plan. The surgeon can have a limited ability to modify the sequence interactively through standard menus, sterilizable computer input devices, and the pointing system. For instance, he could designate where, exactly he has placed (or proposes to place) an osteotomy. The computer could be adapted to simulate this cutting action "online" and allow the surgeon to compare it with the cut proposed when the surgery was planned.

Passive manipulation aids may be provided to assist the surgeon in precisely aligning bone fragments or in aligning his instruments relative to the patient. The defining characteristic of such passive aids is that the surgeon provides all the motive force. Generally, the manipulation aid should interfere as little as possible with the surgeon's tactile "feel" for what is happening to the patient, while preserving the desired alignment once it is achieved. Six degree-of-freedom manipulation aids with manually and semi-automatically actuated brakes have been developed for tissue retraction, instrument placement, and similar applications. One serious drawback of these systems is that they provide little assistance in actually achieving the desired alignment. Even without the additional inertia of a mechanical linkage, most people find it extremely difficult to achieve an accurate six degree-of-freedom alignment. The present invention can use manipulation aids with computer controlled (or manually actuated) brakes to provide selective locking of orthogonally decoupled degrees-of-freedom resolved in a tool frame centered at a point reasonably far removed from the mechanism. This permits implementation of a variety of manipulation strategies in which the surgeon only needs to work on aligning a few (often only one) degrees-of-freedom at a time.

Figure 3:
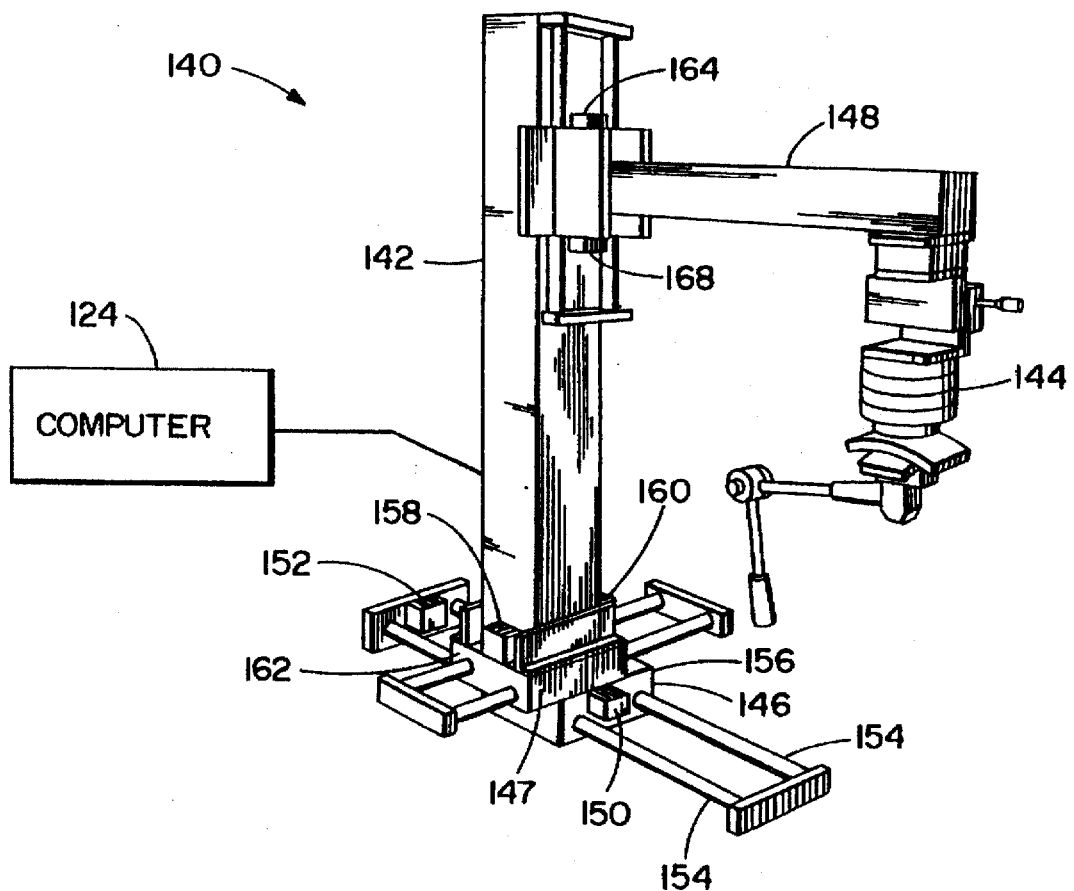
FIG. 3 is a schematic view of an alternate embodiment of the present invention.

Referring now to FIG. 3, there is shown an alternate embodiment of the present invention. The apparatus 140 is similar to the apparatus 10 and comprises a coarse motion manipulator 142 and a fine motion manipulator 144. The coarse motion manipulator 142 is substantially the same as the coarse motion manipulator 12 shown in FIG. 1 and has three links 146, 147 and 148. The fine motion manipulator 144 is substantially identical to the fine motion manipulator 14 shown in FIG. 1. The coarse motion manipulator 142 shown in FIG. 3, unlike the manipulator 14 of FIG. 1, is intended to be computer controlled.

In the embodiment shown, the first link 146 includes a computer controlled driver 150 and a computer controlled brake 152. In an alternate embodiment only the driver 150 need be provided if it is adapted to also function as a brake mechanism. The driver 150 can be any suitable type of electromechanical or electromagnetic drive mechanism, such as a rack and pinion screw type drive mechanism where the rails 154 have screw threads. The driver 150 is thus adapted to move the main block 156 of the first link along the rails 154. The brake 152 may be comprised of any suitable brake mechanism and is generally provided to control the movement of the block 156 on the rails 154. Both the brake 152 and driver 150 are connected to the computer 124 which is adapted to actuate the brake 152 and driver 150 to automatically move the first link 146. In a preferred embodiment, the surgeon can also manually move the first link 146 without use of the driver 150 and the brake 152 can be actuated by the computer to limit or guide movement of the first link 146.

The second link 147 also comprises a computer controlled driver 158 and a computer controlled brake 160 attached to its bottom section 162. The driver 158 and brake 160, which are both connected to the computer 124, control movement of the second link 147 on the first link 146. In the embodiment shown, the second link driver and brake are substantially the same as the first link driver and brake. The third link 148 also comprises a computer controlled driver 164 and computer controlled brake 166. The driver 164 and brake 166, which are both connected to the computer 124, control movement of the third link 148 on the second link 147. In the embodiment shown, the third link driver and brake are substantially the same as the other links' drivers and brakes. However, different types and/or combinations of drivers and brakes could be provided in the coarse motion manipulator 142.

With the embodiment shown in FIG. 3, the computer 124 can move the coarse motion manipulator 142 to automatically move the fine motion manipulator 144 to a location. The surgeon can than use the passive only fine motion manipulator 144 to position and move a surgical instrument connected thereto. This embodiment allows the computer to move the coarse motion manipulator 142 with relatively good speed and accuracy, but nonetheless allows the surgeon fully manual fine motion manipulation via the passive manual only fine motion manipulator 144. Thus, allowing the surgeon to use his skills during fine motion manipulation. As noted above, computer control of the coarse motion manipulator 142 can preferably be manually overriden in the event that the surgeon desires to manually move the coarse motion manipulator 142. In addition, in an alternate embodiment, the drivers 150, 160 and 164 and/or joints between the links 146, 147, 148 have suitable encoders connected to the computer 124 to signal the relative positions of the links relative to each other. The manipulator apparatus 10, in the embodiment shown in FIG. 2, also comprises a force sensor 95 that is adapted to measure the amount of force being applied to the patient by an instrument connected to the apparatus 10. Any suitable force sensor can be used and, the force sensor 95 is adapted to signal the computer 124 of the sensed force to provide force safety monitoring to supplement a surgeon's tactile feedback. This can be especially important when micrometer adjustments are being used.

Figure 4:
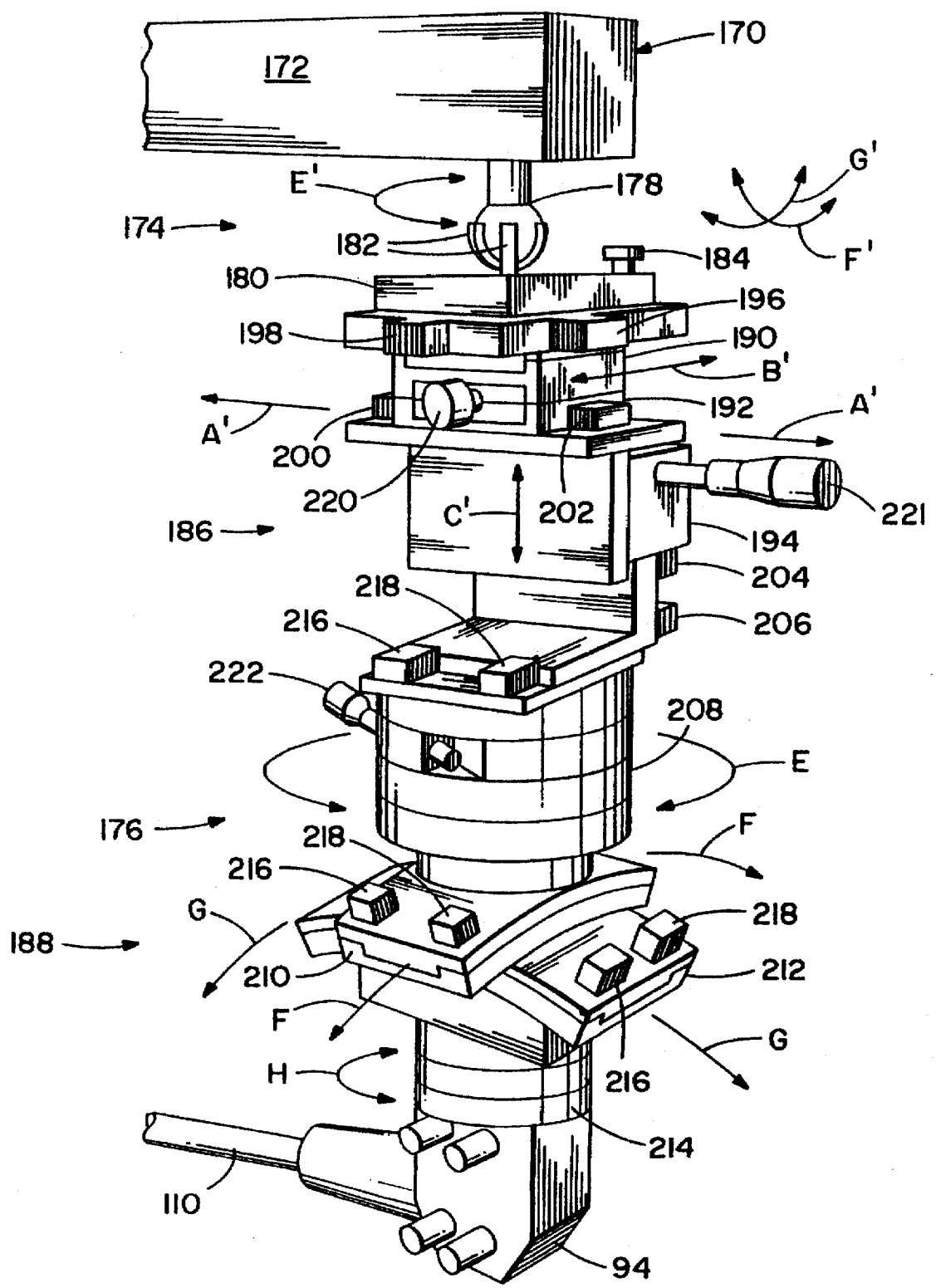
FIG. 4 is a schematic view of an alternate embodiment of the fine motion manipulator of the embodiment shown in FIG. 1 or FIG. 3.

Referring now to FIG. 4, there is shown an alternate embodiment of a distal end of an apparatus similar to those shown in FIGS. 1–3. In the embodiment shown, the distal end 170 of a coarse motion linear manipulator third link 172 has a coarse motion rotational manipulator 174 connected thereto. The fine motion manipulator 176 is connected to the coarse motion rotational manipulator 174. The coarse motion rotational manipulator 174 comprises a ball and socket arrangement with a ball member 178 connected to the distal end 170 and a socket member 180. However, any suitable type of coarse motion rotational manipulator could be provided. The coarse motion rotational manipulator 174 is adapted to provide motion in three revolute degrees-of-freedom as shown by arrows E', F', and G' in FIG. 4. The socket member 180 has friction arms 182 adapted to be pushed against the ball member 178 to lock the two members together and a lock control knob 184 that can be selectively actuated by the surgeon to move the arms 182. Alternatively, a computer controlled driver and/or brake could be provided at the coarse motion rotational manipulator 174 to automatically control rotation, resistance to movement, and locking. The ball-and-socket joint may be used to align the direction of the fine motion axes A', B', and C' in any direction convenient for the surgeon. If desired, this ball-and-socket joint may be replaced by a remote-center-of-motion orthogonally decoupled wrist mechanism similar to rotational section 70.

The fine motion manipulator 176, in the embodiment shown, generally comprises a linear motion section 186 and a rotational motion section 188. The linear motion section 186 is substantially similar to the fine motion manipulator linear motion section described with reference to the embodiment shown in FIG. 1A. The linear motion section 186 has a first section 190, a second section 192, and a third section 194. The first section 190 is connected to the coarse motion rotational manipulator section 174 and is adapted to provide movement in only a single linear path of motion or degree-of-freedom as shown by arrow B'. The first section 190, in the embodiment shown, also comprises a computer controlled driver 196 and a computer controlled brake 198 to control movement of the first section. The second section 192 also comprises a computer controlled driver 200 and a computer controlled brake 202 and, is connected to the first section 190 to provide movement in only a single linear path of motion or degree-of-freedom as shown by arrows A'. The third section 194 is connected to the second section 192 to provide movement in a single linear path of motion or degree-of-freedom as shown by arrow C'. The third section 194 also comprises a computer controlled driver 204 and a computer controlled brake 206.

The rotational motion section 186, in the embodiment shown, generally comprises a first rotation section 208, a second rotation section 210, a third rotation section 212 and a fourth rotation section 214. Thus, the rotational motion section 186 is adapted to provide movement in four revolute degrees-of-freedom. The first, second, and third rotational sections 208, 210, 212 are substantially similar to the rotational manipulator shown in FIG. 1A. However, in the embodiment shown, each of these sections also comprise computer controlled drivers 216 and brakes 218. The fourth section 214 is adapted to provide rotational movement as shown by arrow H to the end member 94 connected thereto that can move the tool 110. The rotational axes of paths E, F, G and H, in the embodiment shown, all intersect at a common point.

Each section in the fine motion manipulator 176 is preferably also manually movable. Both drivers and brakes need not be provided at each section, but may be alternatively provided in different embodiments. In addition, manual actuatable locks, such as locks 220 and 221 can be provided at each section. Micrometer adjustors, such as micrometer 222, may be provided at each section. In a preferred embodiment in which micrometer adjustors are provided, the micrometer adjusters are adapted to provide movement even when a section is locked. The manipulator 176 can be used with a passive only coarse motion manipulator, such as shown in FIG. 1, or a computer controlled coarse motion manipulator, such as shown in FIG. 3. One advantage of the manipulator 176 is that it allows relatively small rotational alignments of an end effector relative to target area by only relatively small rotational movements of the manipulator 176 and, relatively small linear alignments of an end effector relative to target area by only relatively small linear movements of the ,manipulator 176. Another significant advantage of this four degree-of-freedom design is that it makes it easier to fully de-couple the rotational motions in a convenient way. In a three degree-of-freedom wrist, the motions are only really decoupled when rotational motion F is at its approximate center, so that axes $a_E$, $a_F$, and $a_G$ are all mutually perpendicular. With a four axis design, it is possible to align the wrist through a large range of orientations so that axes $a_F$, $a_G$, and $a_H$ are all mutually perpendicular, thus providing three orthogonally decoupled motions. This makes it possible for the surgeon to select a convenient set of rotation axes for performing his task. Computer controlled drivers and/or brakes can allow a surgeon to operate with greater speed and/or accuracy. Although beacons 112 are used on the end member 94 to signal a sensor such as sensor 122 in FIG. 2, joint encoders can also be provided as a redundant means of sensing the position of the end member 94 in the event that the direct line of sight between the beacons 112 and sensor 122 (see FIG. 2) is blocked.

Figure 5:
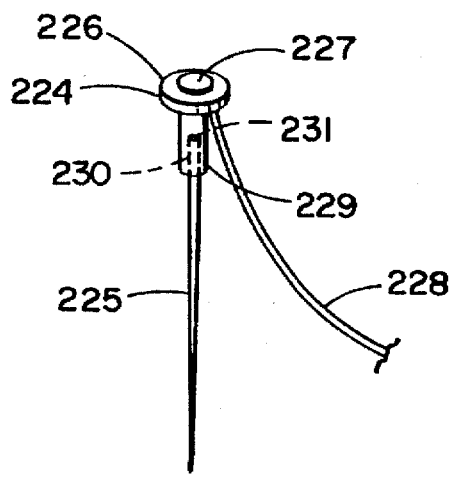
FIG. 5 is a perspective view of a beacon and fixation pin incorporating features of the present invention.

In addition to determining the position of a surgical instrument connected to the apparatus 10 or 140, the optical position sensor system of the present invention is adapted to use beacons to sense and determine the position of a patient, portions of a patient's body, or other surgical instruments and, relative motion of various items. Referring also to FIG. 5, there is shown a beacon 224 and fixation pin 225. The fixation pin 225 is adapted to be fixedly connected to a portion of a patient's body, such as bone. In a preferred embodiment, the pin 225 is a "K-wire" known in the surgical art. The beacon 224 generally comprises a frame 226, a light emitting diode (LED) 227, and an electrical wire 228 connected to the LED. The frame 226 has a channel section 229 adapted to receive or be removably positioned on one end of the pin 225. The channel section 229 has a center channel 230 with an end stop 231. The LED 227 is coaxially aligned over the center channel 230. Because the LED 227 is coaxially aligned over the center channel 230, when the frame 226 is connected to the pin 225, the LED 227 is coaxially aligned with the pin 225. In addition, because the frame channel 230 has an end stop 231, this allows the beacon 224 to be removed from the pin 225 and replaced again on the pin with the LED 227 returning to its same position on the pin as before it was removed. This can obviously give a surgeon greater freedom in an operating room by enabling him to move a beacon and replace it at a later time without risk of causing deviations in position readings by the optical sensor. The center of the visual target will always be located at the same point relative to the pin over which it is attached. In a preferred embodiment, suitable retention means, such as a friction sleeve is provided on the beacon 224 to prevent the beacon 224 from inadvertently slipping of of the end of the pin 225. It should be understood that active beacons are just one possible sort of visual target. Alternative targets could include inactive visual targets, such as spheres or disks, so long as the sensing system can accurately determine the target's three-dimensional location through a reasonably large viewing angle.

Figure 7:
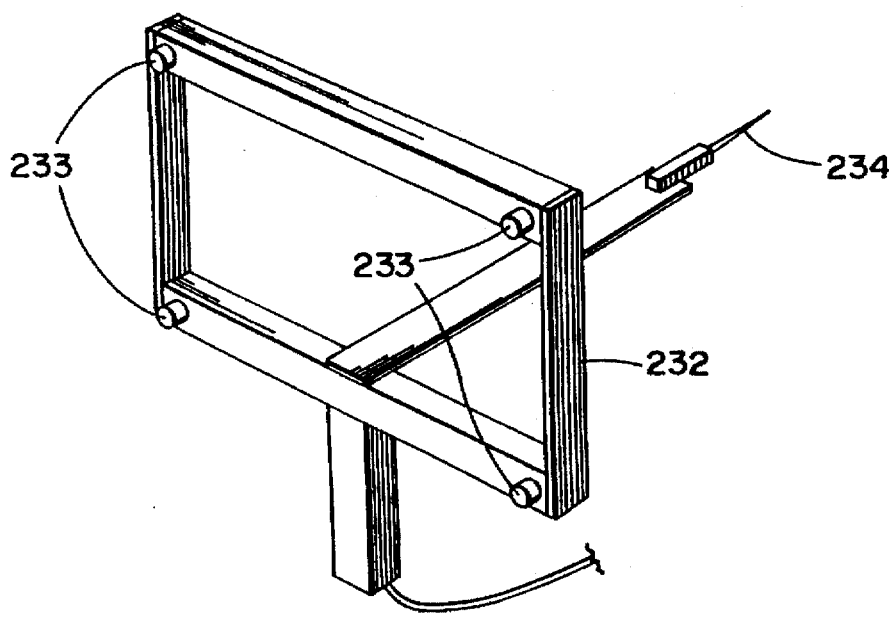
FIG. 7 is a schematic perspective view of a pointer for use in a system incorporating the present invention.
Figure 6:
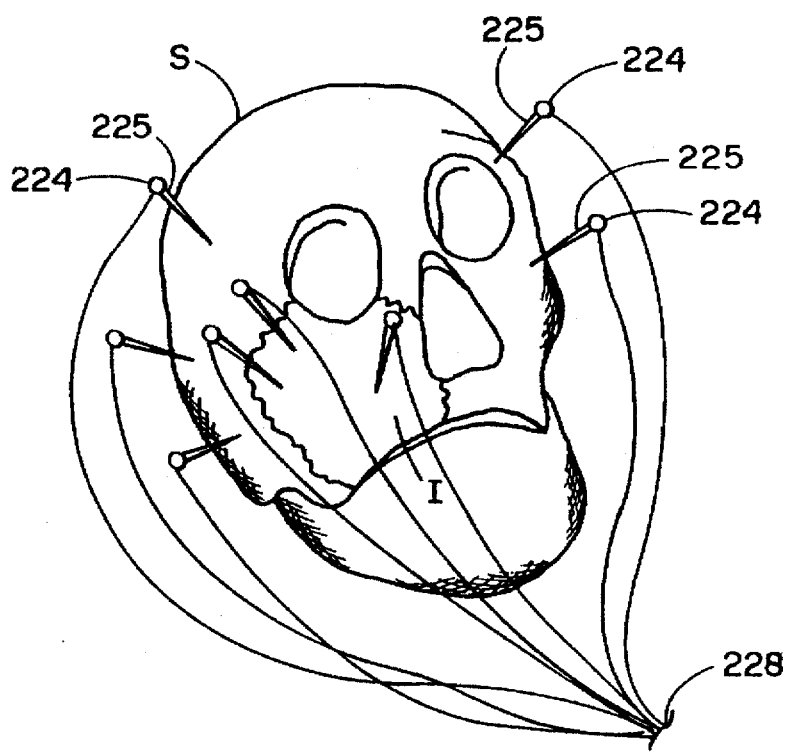
FIG. 6 is a schematic view of beacons for use with the present invention attached to a portion of a patient's anatomy.

Referring now also to FIG. 6, there is shown a schematic view of a patient's skull S having pins 225 connected thereto and beacons 224 mounted to the pins 225. The wires 228 are connected to a computer which controls the timing and/or frequency of illumination of the the beacons' LEDs. In order to determine the position of the beacons 224 relative to the patient's anatomy, in this case the skull S, a pointer 232 as seen in FIG. 7 is used. The pointer 232 has beacons 233 and a pointer tip 234. The surgeon moves the pointer 232 to various landmarks on the patient's skull S and indicates to the computer where the pointer tip 234 is located. The sensor 122 (see FIG. 2) is able to sense the position of the pointer tip 234 from the positions of the beacons 233 and thus, calculates or determines the position of the skull S and the positions of the beacons 224 on the skull. It should be understood that any suitable pointer could be used, or any suitable means for determining the positions of the beacons on the patient's anatomy could be used. Once the positions of the beacons 224 are determined relative to the patient's anatomy, the computer can calculate or determine the relative position of the surgical instrument connected to the apparatus 10 or 140 relative to the patient's body by sensing the positions of the beacons 112 relative to beacons 224.

In addition to sensing the relative positions of a surgical instrument relative to a position of a patient's anatomy, the present invention can be used for positioning a first portion of a patient's body relative to a second portion of a patient's body. This can be particularly usefully in procedures such as reconstructive plastic surgery of a patient's facial skull area. For example, if the bone fragment or piece I was intended to be repositioned relative to the remainder if the skull S, the sensing system of the present invention could sense the positions of the beacons 224 relative to each other. In a preferred embodiment, the computer would already have a surgical plan and optimum position of the bone fragment I. Once the beacon connected to the bone fragment I reaches a predetermined position, the computer would signal the surgeon of the accomplishment. Furthermore, the decoupled degrees of freedom of the manipulation aid permit each degree-of-freedom to be aligned separately and successively, which is much easier than trying to align all degrees-of-freedom simultaneously. Obviously, computer sensing and determining of relative positioning is highly more accurate than merely a surgeon's visual sighting. In a preferred embodiment of the system, the apparatus 10 (see FIG. 1) has a bone clamp adapted to clamp onto the bone fragment I and move the fragment I with computer controlled brakes at each joint of the apparatus 10 to assist the surgeon in fast and accurate relative positioning of the fragment I. Of course, the present invention can be used in any suitable surgical operation.

Figure 8:
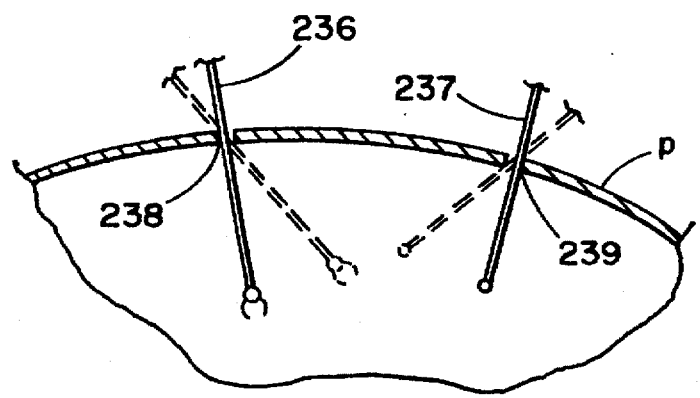
FIG. 8 is a schematic view of an alternate method for using features of the present invention.

Referring now also to FIG. 8, there is shown a schematic view of two surgical instruments 236 and 237 passing through incisions 238 and 239 into a patient's body P and, more specifically, is intended to schematically show a laparoscopic operation. The proximal ends (not shown) of the instruments 236 and 237 are connected to two fine motion rotational manipulators, such as shown in FIG. 4, that can independently move the instruments. Because of the unique motion structure of the fine motion rotational manipulators, the center of rotation for each instrument is located at the incisions 238 and 239 remote from the manipulators. Obviously, in addition to laparoscopy, the system may be readily adapted to arthrosopic or similar surgical procedures in which a surgical instrument must be placed into the patient's body through as incision, body orifice, or other restricted opening, so that little (if any) lateral motion is possible at the point of insertion. Typically in the past, the surgeon's manipulation of the end of the instrument outside the patient's body in order to place the end of instrument inside the body in a desired relationship to the patient's anatomy and/or to other surgical instruments was rather cumbersome and, precise manipulation was very difficult. Often, two people were needed to manually, manipulate instruments (e.g., one person to hold the camera or cameras and one person using both hands to operate two cutting or manipulation instruments).

Figure 9:
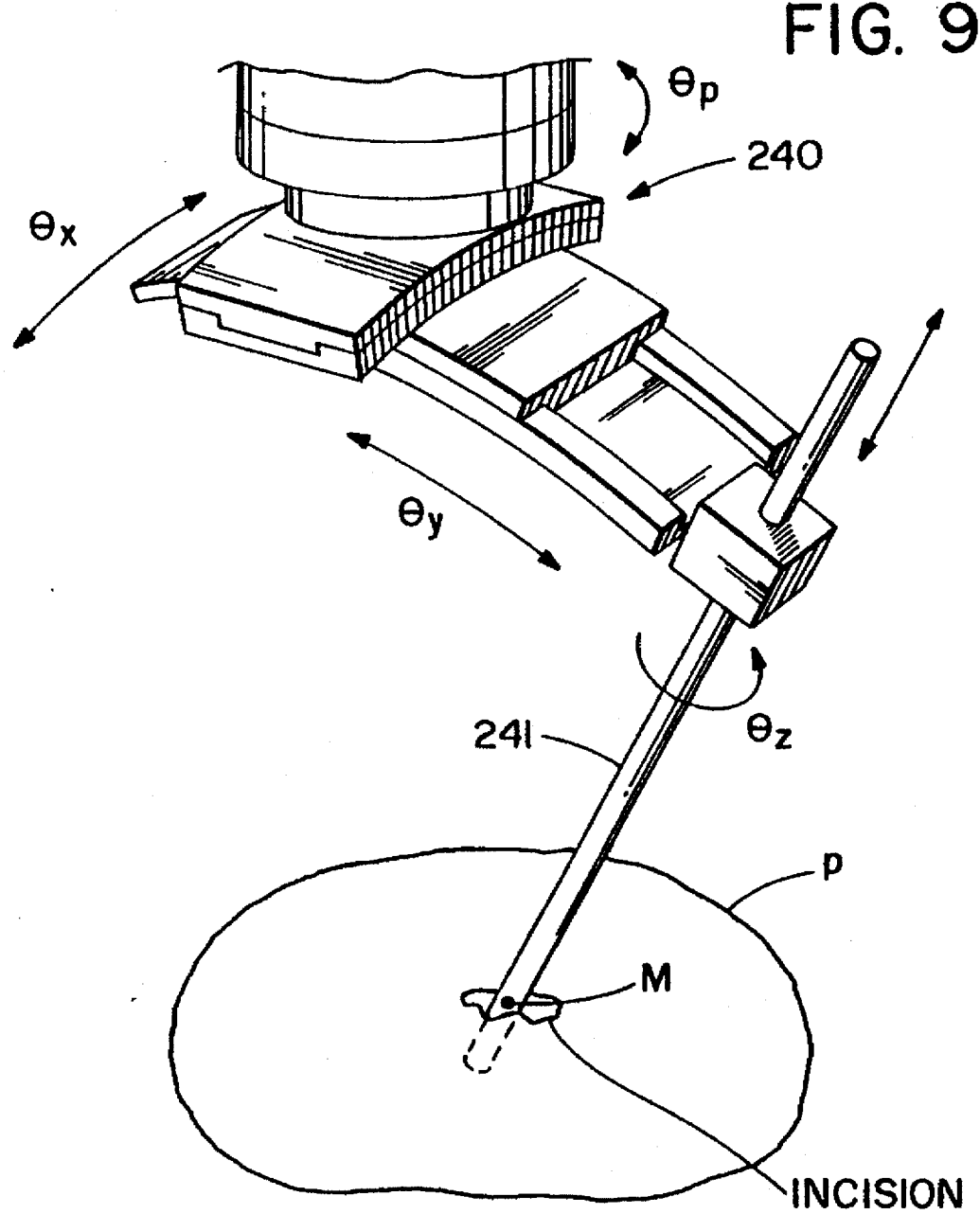
FIG. 9 is a schematic view of a fine motion rotational manipulator with an instrument inserted through an incision into a patient.

Referring also to FIG. 9, there is shown a schematic view of a fine motion rotational manipulator 240 with an instrument 241 inserted through an incision into a patient. In the embodiment shown, the manipulator 240 is adapted to provide axial sliding motion to the instrument 241 to provide a four degree-of-freedom remote center-of-motion wrist, which is supported by a coarse positioning system with three orthogonal linear degrees of freedom. The coarse positioning degrees of freedom are use to place the center-of-motion M of the remote center-of-motion wrist at the point of insertion into the patient's body P. The three most distal revolute degrees-of-freedom and the sliding degree of freedom give the surgeon an orthogonally decoupled four degree-of-freedom spherical work volume centered at the insertion point. These degrees-of-freedom may be selectively locked or moved independently to assist a surgeon in achieving a desired precise alignment. Furthermore, small motions within the four degree-of-freedom work space can be achieved with only small motions of the individual axes. A proximal revolute degree of freedom $\theta_P$ whose motion axes passes throught point M may be used to orient the distal remote center-of-motion axes for maximum convenience. This degree of freedom $\theta_P$ may be moved during the procedure without disturbing the alignment of the manipulator with the point of insertion.

Figure 10:
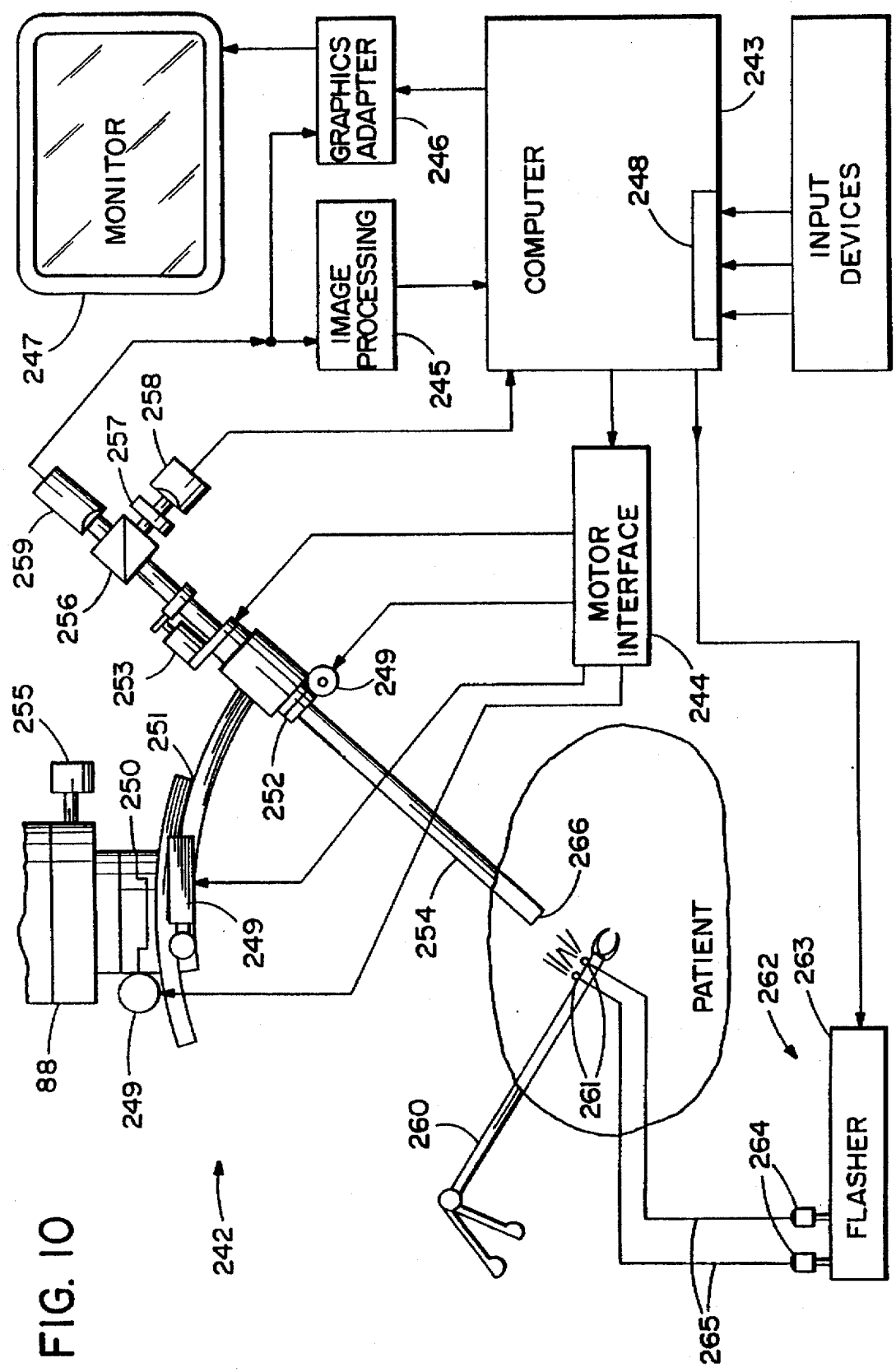
FIG. 10 is a schematic view of a system for use in laparoscopy or similar procedures.

Referring also to FIG. 10, there is shown a schematic view of a system for use in laparoscopy or similar procedures. The system generally comprises a manipulator apparatus 242, a computer 243, a drive motor interface 244, a monitor 247 with a suitable image processor 245 and graphics adaptor 246, and a terminal 248 for connecting additional input devices to the computer 243. The manipulator 242 has drive motors 249 at its three rotational sections 250, 251, and 252 to provide $\theta_x$, $\theta_y$, and distal $\theta_z$ motion and, a slide motor 253 adapted to axially slide the instrument 254. The manipulator 242, in the embodiment shown, also has proximal end X, Y, Z and $\theta_z$ motion capability that can be locked, such as by lock 255. In the embodiment shown, the three most distal revolute axes and the sliding axis are equipped with locks and motorized micrometer fine adjustments. The motors 249 and 253 in turn, are driven through the appropriate interface 244 by computer 243. The instrument 254, in the embodiment shown, includes a splitter 256, a filter 257, a beacon detector 258, a video camera 259, and a suitable image bundle (not shown) to transmit an image from the distal end of the instrument 254 to the splitter 256. The splitter 256 divides the image into two images allowing one image to be received at the camera 259 and, the other image passed through the filter 257 to be received at the beacon detector 258. The video output of the camera 259 is fed into the graphics adaptor 246, where it may be optionally mixed with graphics output from the computer, and is then displayed to the surgeon on monitor 247. The video output of the camera is also optionally fed into image processing system 245 which analyzes the images produced by the camera and provides information to the computer about the relative position of the surgeon's instruments, the camera, and the patient's anatomy. In the embodiment shown, the surgeon is using a second instrument 260 inside the patient's body which has beacons 261 connected thereto. The beacons 261, in the embodiment shown, are comprised of distal ends of fiber optic bundles 265 connected to an illumination system 262 located outside the patient. The illumination system 262 includes a flasher 263 controlled by the computer 243 and LEDs 264. Light is transmitted by the fiber optic bundles 261 to their distal ends on he second instrument 260 where it can be viewed by the first instrument 254.

In the preferred embodiment, the fiber-optic beacons are used to provide readily distinguished targets to facilitate tracking of the surgical instruments. In this case, the LED light sources are bonded to the optical fibers. The distal end of each fiber is bonded in a known place to the surgical instrument to be tracked, and the end is shaped to provide a point source of light visible through a wide angle. Multiple fibers may be bonded to the instrument and may be flashed in succession under control of the computer. The optical splitter 256 diverts a portion of the light passing back through the camera's optical system. This light is passed through a narrow band-pass filter 257 matched to the wavelength of the LED beacons and is imaged onto an appropriate detector 258, which determines the position in the image plane of the centroid of the image of each beacon. From this information, the computer can determine the direction of each point light source to the tip 266 of the camera optical system. From several such point sources, the computer can compute the location and orientation of the surgeon's instrument in the patient's body relative to the tip 266 of the camera optics. Alternatively, the same information may be obtained through standard image processing techniques from the video camera.

The computer can compute appropriate motor commands to move the camera to achieve a desired relationship with the surgeon's instrument. The system can include a method of aligning the manipulator center of motion to a body part and then grabbing the part with an adjustable clamp. In the simplest case, the computer could simply command appropriate $\theta_x$ and $\theta_y$ commands to place the image of a single beacon attached to an instrument at any desired place (e.g. the center) in the video image seen by the video camera. This could be done either in a continuously tracking mode or on command from the surgeon. In more complex cases, the computer would also use the distal $\theta_z$ and sliding motors to provide a "roll" and "zoom" capability.

The surgeon can also use this instrument tracking capability to designate particular anatomical features to the computer or to designate modifications in his surgical plan. The computer can then use this information to modify the graphics display provided to the surgeon, to modify the parameters or algorithms selected for image processing, or in control of additional manipulation aids or system used in surgery. For example, the surgeon may indicate a few points on a blood vessel, bile duct, or other anatomical feature that he wishes to inspect. The computer can then scan the camera over the indicated path while the surgeon devotes his whole attention to the display. Furthermore, the computer can use the designation information to customize image processing algorithms to enhance what the surgeon sees. Clearly, the system described above can be modified for use with surgical instruments other than cameras. For example, a pair of remote-center-of-motion manipulation aids may be used to assist laparoscopic alignment of two anatomical features (e.g., the several ends of a blood vessel or duct) that must be precisely aligned for joining. In one system of the present invention in addition to visually displaying the path of a surgical instrument, the computer can determine a path from a sensed position of the surgical instrument to a target position. The computer can also monitor movement of the surgical instrument and audibly signal deviation from the path. Thus, a surgeon does not need to continuously observe a visual comparison of the determined path and actual path. The audio signals can be provided as different types of signals for different types of occurrences with the computer selecting the appropriate signal based upon a sensed occurrence. The sensing system may also include different sensing modes, such as coarse and fine, and the computer may be adapted to select different sensing modes based upon the sensed position of a surgical instrument relative to a surgical plan, a target area, and/or another surgical instrument, etc. The different sensing modes might also be things such as yaw, pitch, and roll position of the surgical instrument. Thus, the computer could also be adapted to automatically select different types of advice to give the surgeon based upon the surgical plan and the sensed surgical execution. Another system could include means for inputting a change in the surgical plan into the computer during surgery and determining a new surgical plan based, at least partially, upon previously sensed surgical execution of the surgical plan. The means for inputting could include the surgeon moving a surgical instrument to a new position and the means for sensing being adapted to sense the new position and communicate the new position to the means for determining. The means for inputting could be a voice responsive input system. The means for advising could include active advice such as automatically providing resistance force to motion of a surgical instrument in at least one degree-of-freedom, or, automatically moving the surgical instrument.

Let it be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. A system for manipulating movement of a surgical instrument, the system comprising:
    an apparatus having a plurality of motion joints, the apparatus being adapted for manual only driven motion and adapted to have the surgical instrument connected thereto;
    a computer controlled brake located at at least one of the motion joints of the apparatus;
    a computer connected to the brake for selectively actuating the brake upon an occurrence of a predetermined event; and
    means for signaling the computer of the occurrence of the predetermined event.

2. A system as in claim 1 wherein the computer controlled brake is adapted to apply a variable resistance.

3. A system as in claim 2 wherein the means for signaling includes a voice activated system.

4. A system as in claim 2 wherein the means for signaling includes means for optically sensing a position of a beacon.

5. A system as in claim 4 wherein the means for sensing includes redundant sensors at the motion joints in the apparatus.

6. A system as in claim 4 wherein the means for sensing includes at least one beacon connected to the apparatus and a sensor adapted to sense the three dimensional location of the beacon.

7. A system for manipulating movement of a surgical instrument, the system comprising:
    an apparatus adapted to have the surgical instrument connected thereto, the apparatus having a motion joint adapted to be only manually moved by a user;
    a computer controlled brake located at the joint; and
    means for selectively actuating the computer controlled brake.

8. A system as in claim 7 wherein the computer controlled brake and means for selectivity actuating the brake are adapted to apply a variable resistance to motion at the joint.

9. A system as in claim 7 wherein the means for selectively actuating the computer controlled brake includes a computer and a signal for signaling the computer.

* * * * *

UNITED STATES PATENT AND TRADEMARK OFFICE
CERTIFICATE OF CORRECTION

PATENT NO. : 5,695,500
DATED : 12/9/97
INVENTOR(S) : Taylor et al.

It is certified that error appears in the above-identified patent and that said Letters Patent is hereby corrected as shown below:

On the title page, item [75]:

Only one inventor should be listed on the title page of the patent; Russell H. Taylor. Young-yil Kim is not an inventor of the invention recited in the claims of this patent.

Signed and Sealed this

Twenty-seventh Day of July, 1999

*Attest:*

Q. TODD DICKINSON

*Attesting Officer*     *Acting Commissioner of Patents and Trademarks*